United States Patent
Ouyang

(10) Patent No.: US 11,558,934 B2
(45) Date of Patent: Jan. 17, 2023

(54) ATOMIZER AND ELECTRONIC CIGARETTE HAVING SAME

(71) Applicant: SHENZHEN IVPS TECHNOLOGY CO., LTD., Shenzhen (CN)

(72) Inventor: Junwei Ouyang, Shenzhen (CN)

(73) Assignee: SHENZHEN IVPS TECHNOLOGY CO., LTD., Shenzhen (CN)

( * ) Notice: Subject to any disclaimer, the term of this patent is extended or adjusted under 35 U.S.C. 154(b) by 699 days.

(21) Appl. No.: 16/527,061

(22) Filed: Jul. 31, 2019

(65) Prior Publication Data
US 2020/0077704 A1 Mar. 12, 2020

(30) Foreign Application Priority Data

Sep. 12, 2018 (CN) .......................... 201821493055.0

(51) Int. Cl.
*A24F 47/00* (2020.01)
*H05B 3/06* (2006.01)
*H05B 3/44* (2006.01)
*F16J 15/02* (2006.01)
*A24F 40/40* (2020.01)
*A24F 40/10* (2020.01)

(52) U.S. Cl.
CPC .............. *H05B 3/06* (2013.01); *A24F 40/40* (2020.01); *F16J 15/022* (2013.01); *H05B 3/44* (2013.01); *A24F 40/10* (2020.01); *H05B 2203/016* (2013.01); *H05B 2203/021* (2013.01)

(58) Field of Classification Search
None
See application file for complete search history.

(56) References Cited

U.S. PATENT DOCUMENTS

| | | | |
|---|---|---|---|
| 9,993,028 B2* | 6/2018 | Li | A24F 40/44 |
| 11,123,501 B2* | 9/2021 | Nettenstrom | A61M 11/042 |
| 2018/0338538 A1* | 11/2018 | Zheng | H05B 1/0227 |
| 2019/0053542 A1* | 2/2019 | Chen | A61M 11/042 |
| 2019/0083720 A1* | 3/2019 | Leadley | A61M 11/042 |
| 2019/0098931 A1* | 4/2019 | Leadley | A24F 40/40 |

(Continued)

FOREIGN PATENT DOCUMENTS

| CN | 203341007 U | 12/2013 |
|---|---|---|
| EP | 3360430 A | 8/2018 |
| WO | 2017163045 A | 9/2017 |

*Primary Examiner* — Joseph M. Pelham
(74) *Attorney, Agent, or Firm* — IP-PAL Patent US; Klaus Michael Schmid

(57) ABSTRACT

An atomizer for an electronic cigarette and an electronic cigarette are presented. The atomizer comprises a substrate, a heating device and a cover member. The substrate is provided with a mounting space. One end of the heating device is inserted into the mounting space and partially extends to the outside through the substrate to form a controlling member, and the other end is exposed to the outer surface of the substrate. When the controlling member is pressed into the substrate by an external pressing force, the heating device is pushed to move toward the outside of the substrate along the mounting space and partially extends out of the substrate. The cover member is detachably mounted to the substrate and covers the controlling member. The technical solution of the present invention is convenient for the user to disassemble and replace the heating device inside the atomizer, effectively saving the use cost.

14 Claims, 5 Drawing Sheets

(56) References Cited

U.S. PATENT DOCUMENTS

| | | | |
|---|---|---|---|
| 2019/0099561 A1* | 4/2019 | Nettenstrom | A61M 11/042 |
| 2019/0191764 A1* | 6/2019 | Lin | A24F 40/40 |
| 2020/0375263 A1* | 12/2020 | Chen | A61M 21/00 |
| 2021/0045444 A1* | 2/2021 | Liu | A24F 40/50 |
| 2021/0401044 A1* | 12/2021 | Qiu | A24F 40/10 |

* cited by examiner

ATOMIZER AND ELECTRONIC CIGARETTE HAVING SAME

TECHNICAL FIELD

The present invention relates to an atomizer for an electronic cigarette and an electronic cigarette using the atomizer for the electronic cigarette.

BACKGROUND

Electronic cigarettes, also known as e-cigarettes or e-cigs, are mainly used to quit smoking and replace conventional cigarettes. E-cigs have an appearance and taste that is similar to conventional cigarettes, and even offer a wider range of flavors than conventional cigarettes. E-cigs can generate vapor with a similar taste and experience like conventional cigarettes. Without tar, particles, and other harmful components in conventional cigarettes, electronic cigarettes have gradually replaced conventional cigarettes in the market.

The existing atomizer for small electronic cigarettes is usually provided with an oil storage chamber and a heating device therein, and then is provided with an oil guiding cotton (i.e., a wick) to adsorb tobacco liquid in the oil storage chamber to the heating device for atomizing, thereby generating smoke for users to inhale. However, during long-term use, the oil guiding cotton is easily burned or carbonized from the heat generated by the heating device, resulting in greater harm on the human body over time. However, with current atomizers of small electronic cigarettes, it is generally not possible to remove the internal heating device from the atomizer thus only the entire atomizer can be replaced.

SUMMARY

The main purpose of the present invention is to provide an atomizer for an electronic cigarette, which is convenient for the user to disassemble and replace the heating device inside the atomizer, thereby effectively saving cost and waste, while preserving the user experience.

In order to achieve the above object, the present invention provides an atomizer for an electronic cigarette, comprising: a base housing body, a heating device, and a cover member, wherein the base housing body defines a mounting cavity, one end of the heating device is inserted into the mounting cavity and partially extends to the outside through the base housing body to form a manipulation piece, and the other end is exposed to the outer surface of the base housing body, when the manipulation piece is pressed into the base housing body by an external pressing force, the heating device is pushed to move toward the outside of the base housing body along the mounting cavity and partially extends out of the base housing body, and the cover member is detachably mounted to the base housing body and covers the manipulation piece.

Optionally, the cover member is further provided with a connecting portion, when the cover member is mounted to the base housing body, the connecting portion is engaged with the manipulation piece for fixedly connecting the cover member with the manipulation piece, and when the cover member is separated from the base housing body, the manipulation piece is disengaged from the connecting portion.

Optionally, one of the connecting portion and the manipulation piece is provided with an engaging groove, and the other of the connecting portion and the manipulation piece is provided with a first elastic sealing ring on a part of the outer peripheral surface thereof, so that the sealing ring abuts the inner groove wall of the engaging groove when being engaged into the engaging groove.

Optionally, a step-shaped limiting portion is formed at a transition between the heating device and the manipulation piece, the base housing body is correspondingly provided with an exit hole and a limiting groove into which a part of the limiting portion is engaged, when the heating device is mounted to the mounting cavity, the manipulation piece extends out of the base housing body through the exit hole, and the limiting portion is elastically clamped in the limiting groove, so that the heating device is limited to the mounting cavity.

Optionally, the end of the heating device away from the manipulation piece is further provided with an elastic limiting seat, and when the heating device is mounted to the mounting cavity, an outer peripheral surface of the limiting seat abuts an inner wall of the mounting cavity, so that the heating device is limited to the base housing body.

Optionally, the base housing body is further provided with a tapered supporting member at both sides adjacent to the manipulation piece, and the outer peripheral surface of the tapered supporting member is closely fitted to the inner wall of the cover member so that the cover member is fixedly mounted to the base housing body.

Optionally, the thickness of the tapered supporting member is gradually increased from the end of the tapered supporting member away from the base housing body toward the end of the base housing body; and/or the tapered supporting member is provided with two notches in the engaging direction in which the base housing body is inserted into the cover member, so that when the cover member is mounted to the base housing body, the outer surface of the tapered supporting member is pressed to be elastically deformed toward the two notches.

Optionally, the cover member is provided with two air inlets, the two notches are communicated with the outside airflow through the two air inlets, respectively, the base housing body is provided with an airflow passage, one end of the airflow passage is communicated with the two notches, and the other end is communicated with an internal chamber of the heating device for providing a working airflow to the heating device.

Optionally, the base housing body is provided with an oil storage chamber arranged within the mounting cavity, the heating device comprises a heating base and an air outlet pipe, the heating base is provided with an atomizing chamber in fluid communication with the airflow passage and an oil guiding hole communicated with the atomizing chamber, the air outlet pipe is mounted to the heating base and is communicated with the atomizing chamber, when the heating device is mounted to the mounting cavity, the oil guiding hole is in fluid communication with the oil storage chamber, and the air outlet pipe extends out of the base housing body to form the manipulation piece.

The present invention also provides an electronic cigarette, comprising an atomizer for an electronic cigarette, wherein the atomizer comprises a base housing body, a heating device, and a cover member, wherein the base housing body is provided with a mounting cavity, one end of the heating device is inserted into the mounting cavity and partially extends to the outside through the base housing body to form a manipulation piece, and the other end is exposed to the outer surface of the base housing body, when the manipulation piece is pressed into the base housing body by an external pressing force, the heating device is pushed to move toward the outside of the base housing body along the mounting cavity and partially extends out of the base housing body, and the cover member is detachably mounted to the base housing body and covers the manipulation piece.

According to the atomizer for the electronic cigarette according to the technical solution of the present invention, the base housing body defines a mounting cavity, the heating device of the atomizer is engaged into the mounting cavity to form an assembling member with the base housing body, and one end of the heating device is exposed to the outside through the base housing body to form a controlling portion. When the heating device inside the atomizer is damaged and needs to be replaced, only the manipulation piece needs to be pressed, so that the manipulation piece pushes the heating device to move toward the outside of the base housing body along the mounting cavity to extend out of the base housing body, and then is pulled out. A new heating device is then inserted into the mounting cavity so as to complete the replacement. The operation is simple and cost effective by only replacing the heating device inside the atomizer. At the same time, a cover member detachably mounted to the base housing body is provided, so that the manipulation piece is covered during normal use, effectively preventing the phenomenon that the manipulation piece is mishandled by an external pressing force when the electronic cigarette is put into the pocket.

BRIEF DESCRIPTION OF THE DRAWINGS

For a better illustration of the embodiments of the present invention or the technical solution in the prior art, accompanying drawings needed in the description of the embodiments or the prior art are simply illustrated below. Obviously, the accompanying drawings described below are some embodiments of the present invention. For those skilled in the art, other accompanying drawings may be obtained according to the structure shown in these accompanying drawings without creative work.

DESCRIPTION OF THE REFERENCE NUMBERS

Figure 1:
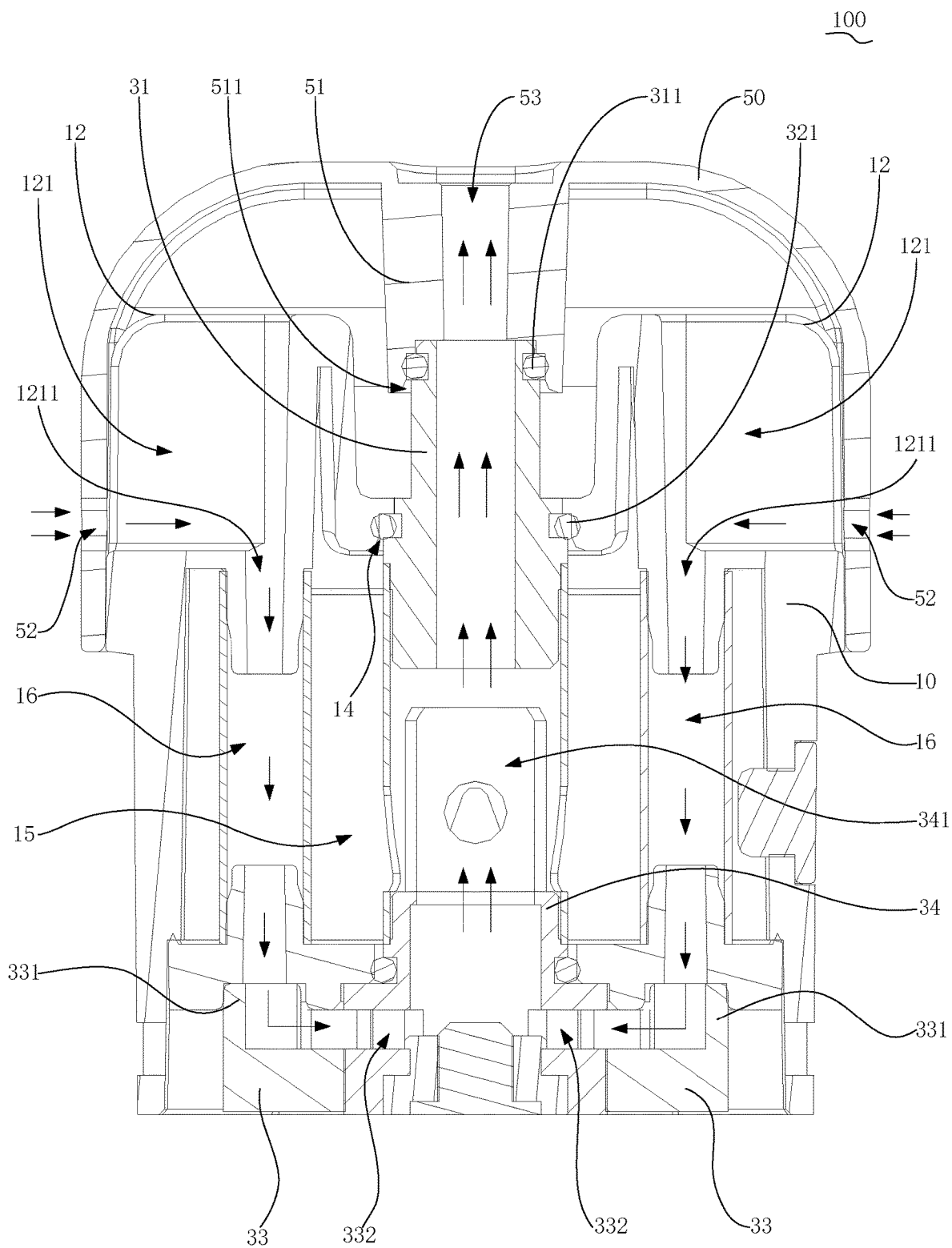
FIG. 1 is a cross-sectional schematic diagram illustrating a connecting structure of an atomizer for an electronic cigarette according to the present invention.

| Reference number | Name of part |
| --- | --- |
| 100 | atomizer |
| 10 | substrate |
| 11 | mounting space |
| 12 | supporting member |
| 121 | notch |
| 1211 | air passing hole |
| 13 | avoidance hole |
| 14 | limiting groove |

-continued

| Reference number | Name of part |
| --- | --- |
| 15 | oil storage chamber |
| 16 | airflow passage |
| 30 | heating device |
| 31 | controlling member |
| 311 | first sealing ring |
| 32 | limiting portion |
| 321 | second sealing ring |
| 33 | limiting seat |
| 331 | air guiding column |
| 332 | air inlet passage |
| 34 | heating base |
| 341 | atomizing chamber |
| 342 | oil guiding hole |
| 343 | air inlet |
| 50 | cover member |
| 51 | connecting portion |
| 511 | engaging groove |
| 52 | air inlet |
| 53 | suction port |
| 1000 | electronic cigarette |

The implementation of aims, the function features and the advantages of the present disclosure are described below in further detail in conjunction with embodiments with reference to the drawings.

DESCRIPTION OF THE EMBODIMENTS

A clear and complete description as below is provided for the technical solution in the embodiments of the present invention in conjunction with the drawings in the embodiments of the present invention. Obviously, the embodiments described hereafter are simply part embodiments of the present invention, rather than all the embodiments. All other embodiments obtained by those skilled in the art based on the embodiments in the present invention without creative work are intended to be included in the scope of protection of the present invention.

It should be noted that all directional indications (such as top, bottom, left, right, front, behind . . . ) in the embodiments of the present invention are merely to illustrate a relative position relation, a relative motion condition, etc. between each part in a certain state (for example, the state shown in the drawings). If the state changes, the directional indication changes accordingly.

In addition, if terms "first", "second", etc. appear in the present invention, they are merely for the purpose of description, but cannot be understood as the indication or implication of relative importance or as the implicit indication of the number of the designated technical features; therefore, features defined by "first" and "second" may specifically or implicitly comprise at least one such feature. In addition, technical solutions of each embodiment of the present invention may be combined mutually; however, this must be carried out on the basis that those skilled in the art can implement the combination. When the combination of technical solutions has a conflict or cannot be implemented, it should be considered that such combination of technical solutions does not exist and is not in the scope of protection claimed by the present invention.

In the present invention, unless otherwise specifically stated and defined, terms "connected", "fixed", etc. should be interpreted expansively. For example, "fixed" may be fixed connection, detachable connection, or integration; may be mechanical connection or electrical connection; direct connection, indirect connection through an intermediate, or internal communication between two elements or interaction of two elements, unless otherwise specifically defined. Those skilled in the art can understand the specific implication of the above terms in the present invention according to specific conditions.

The present invention provides an electronic cigarette 1000. The electronic cigarette 1000 comprises an atomizer 100 and a battery device for supplying power to the atomizer 100. The battery device is provided with a mounting chamber into which the atomizer 100 is engaged, the atomizer 100 is engaged into the mounting chamber to establish an electrical connection with the battery device, and the atomizing device includes an airflow channel 16, a heating device 30, and a receiving chamber configured to store tobacco products. The heating device 30 heats the adsorbed tobacco liquid when being driven by the electric power of the battery device to generate smoke for the user to smoke after the smoke flows out through the airflow passage. Here, the tobacco product may be selected from the group consisting of tobacco liquid, tobacco paste, flake-shaped tobacco filament, block-shaped tobacco filament, or a tobacco pellet or a cigarette processed from tobacco filament. In an embodiment of the present invention, the tobacco product is selected from tobacco liquid.

Referring to FIG. 1 to FIG. 5, in the embodiment of the present invention, the atomizer 100 of the electronic cigarette 1000 comprises a base housing body 10, a heating device 30, and a cover member 50, wherein the base housing body 10 defines a mounting cavity 11, one end of the heating device 30 is inserted into the mounting cavity 11 and partially extends to the outside through the base housing body 10 to form a manipulation piece 31, and the other end is exposed to the outer surface of the base housing body 10, when the manipulation piece 31 is pressed into the base housing body 10 by an external pressing force, the heating device 30 is pushed to move toward the outside of the base housing body 10 along the mounting cavity 11 and partially extends out of the base housing body 10, and the cover member 50 is detachably mounted to the base housing body 10 and covers the manipulation piece 31.

According to a technical solution of the present invention, the base housing body 10 defines a mounting cavity 11, the heating device 30 of the atomizer 100 is engaged into the mounting cavity 11 to form an assembling member with the base housing body 10, and one end of the heating device 30 is exposed to the outside through the base housing body 10 to form a controlling portion. When the heating device 30 inside the atomizer 100 is damaged and needs to be replaced, only the controlling portion needs to be pressed, so that the controlling portion pushes the heating device 30 to move toward the outside of the base housing body 10 along the mounting cavity 11 to extend out of the base housing body 10, and then is pulled out. A new heating device 30 is then inserted along the mounting cavity 11 so as to complete the replacement. The operation is simple and cost effective by only replacing the heating device 30 inside the atomizer 100. Further, a cover member 50 (e.g., a mouthpiece) that is detachably mounted to the base housing body 10 is provided, so that the manipulation piece 31 is covered during normal use, effectively preventing the phenomenon that the manipulation piece 31 is mishandled by an external pressing force when the electronic cigarette 1000 is put into a pocket.

Further, as shown in FIG. 1, in the embodiment of the present invention, the cover member 50 is further provided with a connecting portion 51, when the cover member 50 is mounted to the base housing body 10, the connecting portion 51 is engaged with the manipulation piece 31 for coupling the cover member 50 with the manipulation piece 31, and when the cover member 50 is separated from the base housing body 10, the manipulation piece 31 is disengaged from the connecting portion 51. Here, in the present embodiment, the cover member 50 defines a connecting portion 51 so as for coupling with the manipulation piece 31 of the heating device 30 when the cover member 50 is mounted to the base housing body 10, effectively enhancing the stability of the connection between the heating device 30 and the base housing body 10, and preventing the heating device 30 from directly abutting along a portion of the mounting cavity 11, which results in a gap during a long-term use so that the heating device 30 is directly disengaged from the base housing body 10.

Specifically, as shown in FIG. 1, in the embodiment of the present invention, one of the connecting portion 51 and the manipulation piece 31 is provided with an engaging groove 511, and the other of the connecting portion 51 and the manipulation piece 31 is provided with a first elastic sealing ring 311 on a part of the outer peripheral surface thereof, so that the sealing ring abuts the inner groove wall of the engaging groove 511 when being engaged into the engaging groove 511. Here, in the present embodiment, the connecting portion 51 is provided with an engaging groove 511. The end of the manipulation piece 31 away from the heating device 30 is provided with a groove at the outer circumference thereof into which the first sealing ring 311 is sleeved. When the extending end of the connecting portion 51 is inserted into the engaging groove 511, the first sealing ring 311 is deformed by the pressing force of the inner wall of the engaging groove 511 to be closely fitted and fixed to the groove wall of the inner circumference of the engaging groove 511. At the same time, the elastic interference fit is adopted, which is convenient for the user to pull out the cover member 50.

Figure 2:
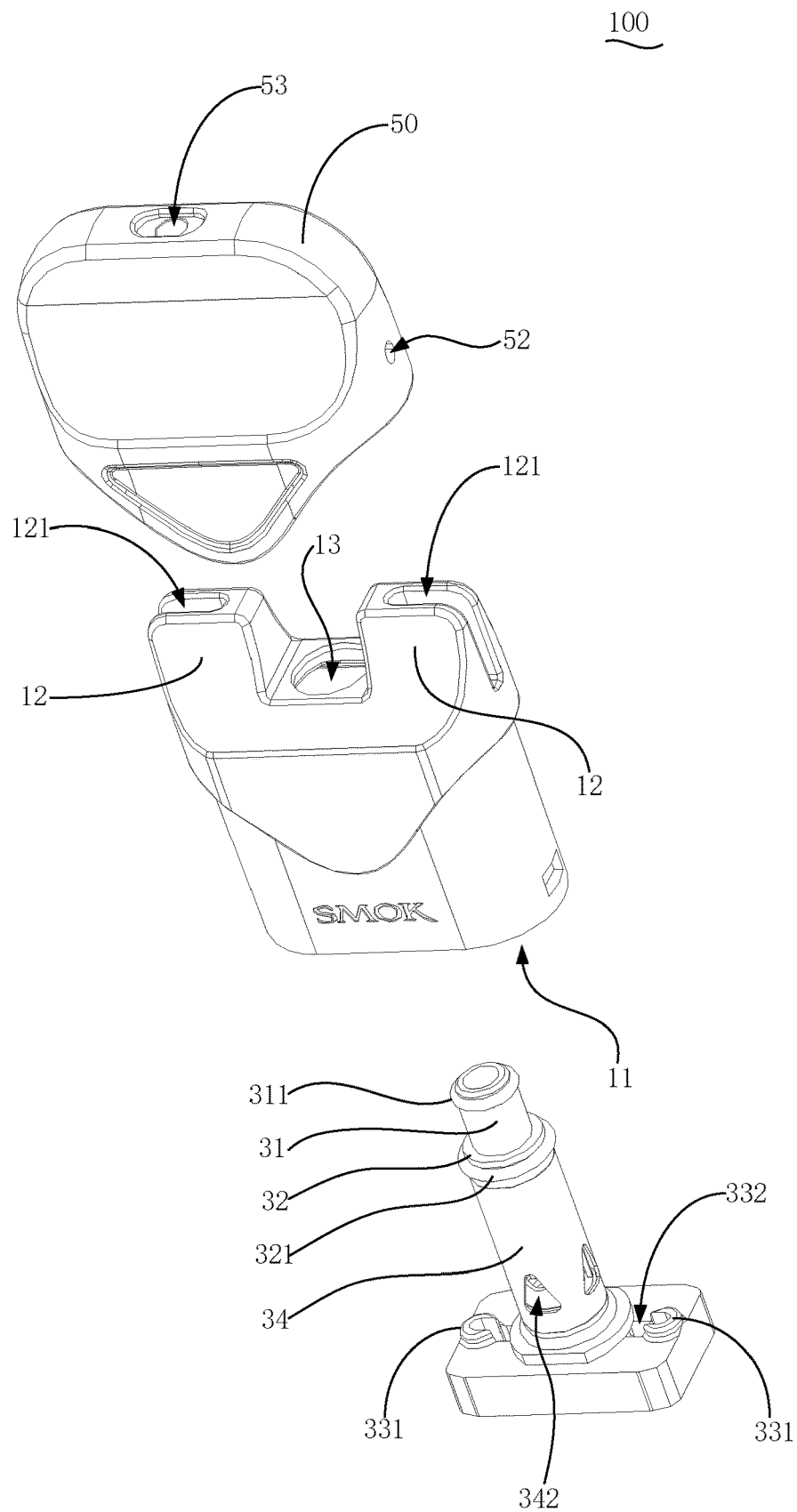
FIG. 2 is an exploded schematic diagram illustrating a connecting structure of an atomizer for an electronic cigarette according to the present invention.
Figure 3:
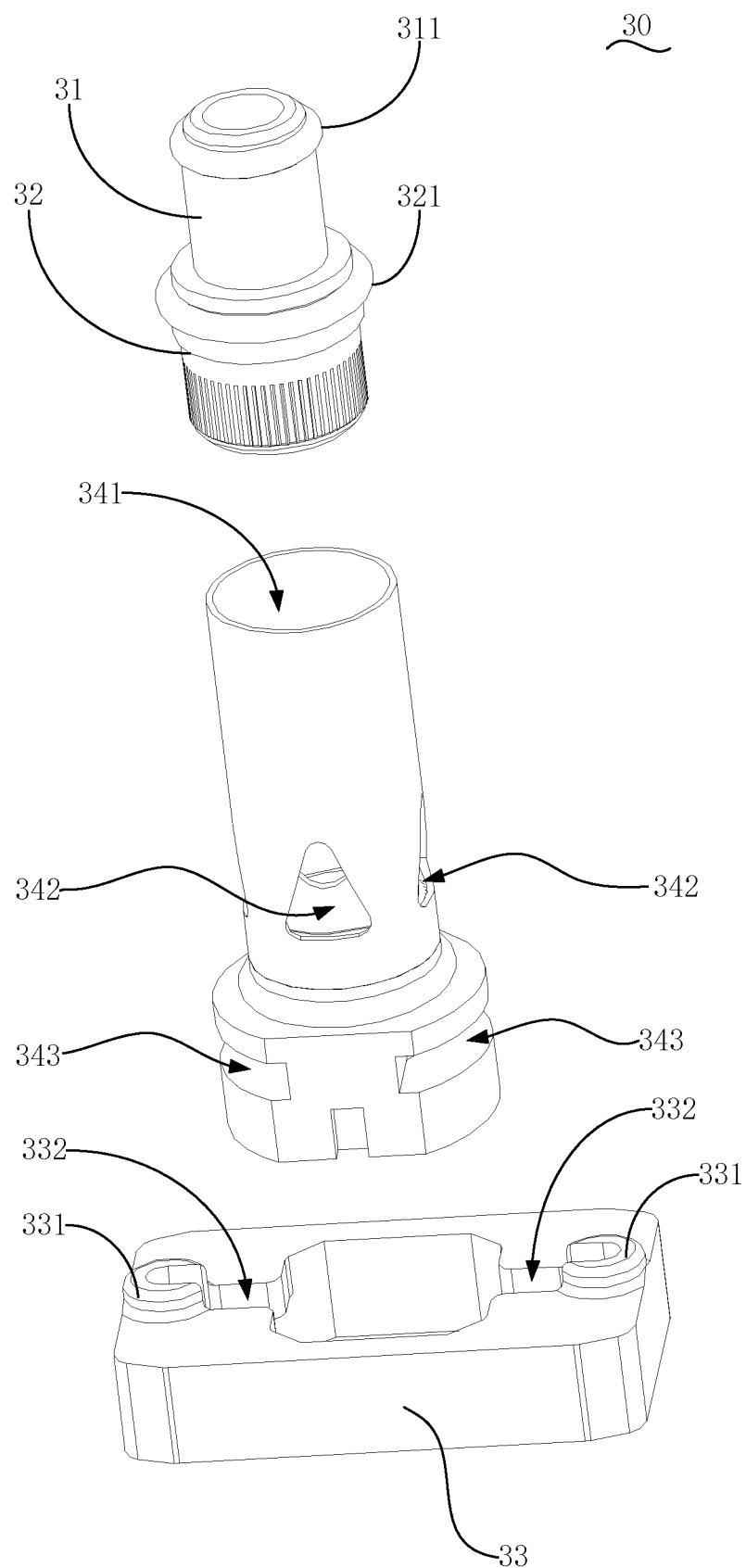
FIG. 3 is an exploded schematic diagram illustrating a connecting structure of a heating device according to the present invention.

Specifically, as shown in FIG. 2 or FIG. 3, in the embodiment of the present invention, a stepped limiting portion 32 is formed at a transition between the heating device 30 and the manipulation piece 31, the base housing body 10 is correspondingly provided with an exit hole 13 and a limiting groove 14 into which a part of the limiting portion 32 is engaged, when the heating device 30 is mounted to the mounting cavity 11, the manipulation piece 31 extends out of the base housing body 10 through the exit hole 13, and the limiting portion 32 is elastically clamped in the limiting groove 14, so that the heating device 30 is limited to the mounting cavity 11. Here, in the present embodiment, the manipulation piece 31 is provided on the extending main body of the heating device 30, a stepped limiting portion 32 is formed at a transition between the heating device 30 and the manipulation piece 31, and a neck is provided in the limiting portion 32. A second elastic sealing ring 321 is sleeved in the neck. One end of the manipulation piece 31 is received in the outside of the base housing body 10 through the exit hole 13, the limiting portion 32 formed by the extending head end of the manipulation piece 31 is engaged into the limiting groove 14, and the second sealing ring 321 is fitted to the inner groove wall surface of the limiting groove 14 and is elastically clamped in the limiting groove 14, so that the heating device 30 is detachably mounted in the mounting cavity 11. The connection is relatively stable and external dust is effectively prevented from flowing into the mounting cavity 11 through the exit hole 13. When the disassembly is required, the manipulation piece 31 only needs to be pressed to move the manipulation piece 31 to the inside of the mounting cavity 11, so that the limiting portion 32 sleeved with the second sealing ring 321 is disengaged from the limiting groove 14, and the heating device 30 is pulled out from the base housing body 10. No screws, snaps or threads are required for fixing, which is convenient to mount and disassemble.

Further, as shown in FIG. 3, in the embodiment of the present invention, the end of the heating device 30 away from the manipulation piece 31 is further provided with an elastic limiting seat 33, and when the heating device 30 is mounted to the mounting cavity 11, an outer peripheral surface of the limiting seat 33 abuts an inner wall of the mounting cavity 11, so that the heating device 30 is limited to the base housing body 10. Here, in the present embodiment, the end of the heating device 30 away from the limiting portion 32 is sleeved with the limiting seat 33. The limiting seat 33 may be made of elastic silicone or elastic plastic. In the present embodiment, the elastic silicone is used. The outer peripheral surface of the limiting seat 33 is fitted to the inner wall of the mounting cavity 11 and is elastically abutted against the inner wall of the mounting cavity 11. The end of the heating device 30 provided with the manipulation piece 31 and the end opposite to the manipulation piece 31 are elastically clamped to the base housing body 10 to further enhance the connection strength between the heating device 30 and the base housing body 10, preventing the phenomenon that the heating device 30 is disengaged from the base housing body 10 by the small external force.

Specifically, as shown in FIG. 2, in the embodiment of the present invention, the base housing body 10 further defines tapered supporting members 12 at both sides adjacent to the manipulation piece 31, and the outer peripheral surface of the tapered supporting member 12 is closely fitted to the inner wall of the cover member 50 so that the cover member 50 is fixedly mounted to the base housing body 10. Here, in the present embodiment, the base housing body 10 is further defines a tapered supporting member 12 at both sides adjacent to the manipulation piece 31. A supporting space is formed between the two tapered supporting members 12, and the surface of the extending end of a tapered supporting member 12 is flush with or higher than the surface of the manipulation piece 31 extending beyond the base housing body 10, so that the manipulation piece 31 is received in the supporting space. When the cover member 50 is disengaged from the base housing body 10, if the pressing force applied by the manipulation piece 31 is biased, or the applied force has a large area, the object that applies the external pressure is abutted against the tapered supporting member 12 to restrict the pressing force from being applied on the manipulation piece 31, thereby effectively preventing the phenomenon that when the cover member 50 is disengaged from the base housing body 10, the manipulation piece 31 is placed in the pocket and is erroneously pressed into the base housing body 10 by the external pressing force so that the heating device 30 is disengaged from the base housing body 10. At the same time, the outer peripheral surface of the tapered supporting member 12 is closely fitted to the inner wall of the cover member 50, effectively reinforcing the friction between the cover member 50 and the tapered supporting member 12, thereby enhancing the connection strength between cover member 50 and the base housing body 10, and preventing the phenomenon that the cover is disengaged from the base housing body 10 by a small external force.

Figure 4:
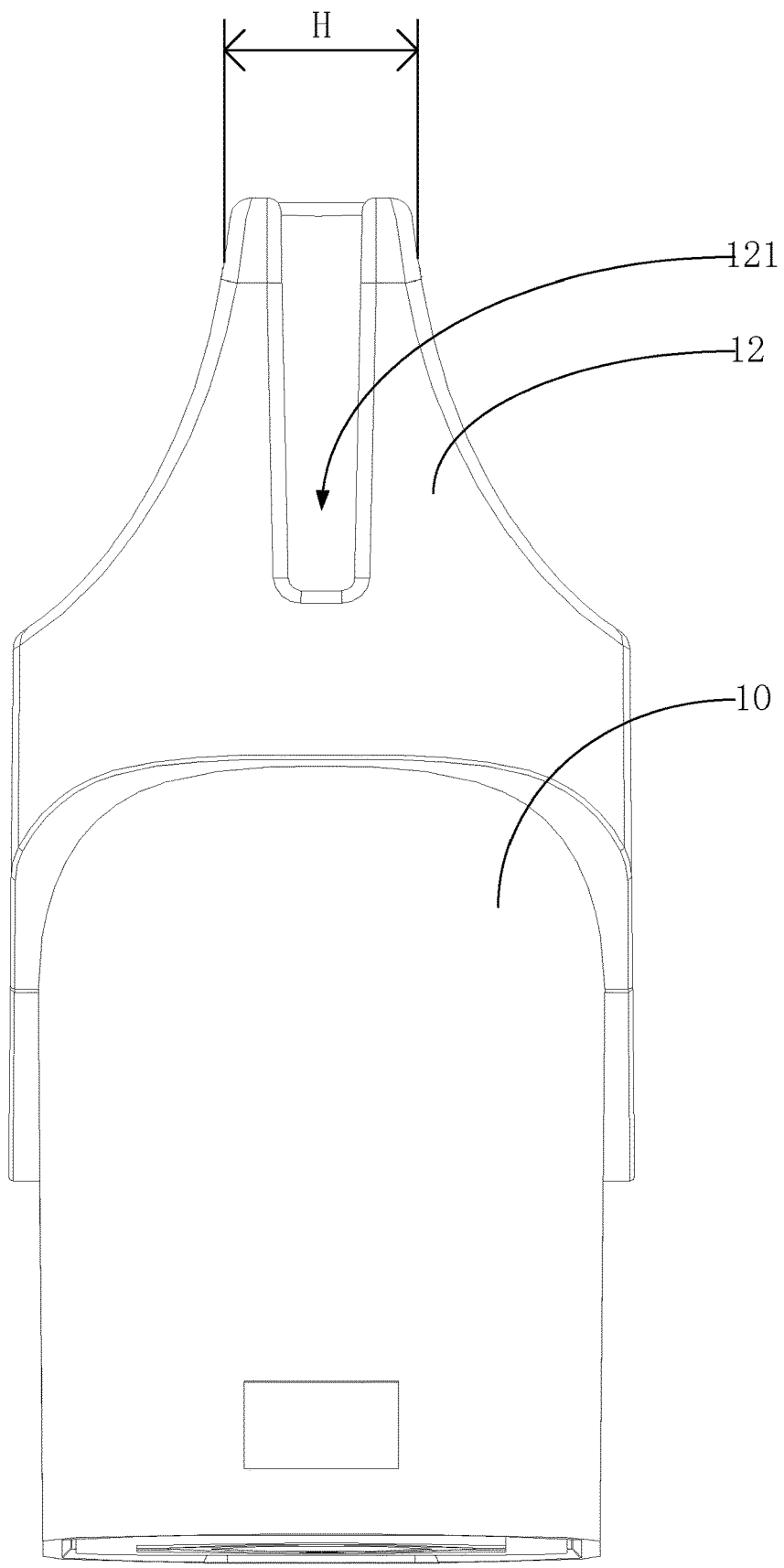
FIG. 4 is a perspective schematic diagram illustrating a connecting structure of an electronic cigarette according to the present invention.

Specifically, as shown in FIG. 4, in the embodiment of the present invention, the thickness of the tapered supporting member 12 is gradually increased from the end of the tapered supporting member 12 away from the base housing body 10 and towards the end of the base housing body 10; here, in the present embodiment, the tapered supporting member 12 is integrally formed with the base housing body 10, and while the tapered supporting member 12 is extended outwardly from one end of the base housing body 10, the thickness value H of the tapered supporting member 12 is gradually reduced and the overall shape is curved. When the base housing body 10 is inserted into the inner chamber of the cover member 50, the end of the tapered supporting member 12 having a small thickness is first inserted into the cover member 50. As the base housing body 10 is gradually inserted into the cover member 50, the thickness of the tapered supporting member 12 is gradually increased, so that the outer peripheral surface of the tapered supporting member 12 is gradually closely fitted to the inner wall of the cover member 50, which is convenient for the user to mount and disassemble.

Further, as shown in FIG. 1 or FIG. 2, in the embodiment of the present invention, the tapered supporting member 12 is provided with two notches 121 in the engaging direction in which the base housing body 10 is inserted into the cover member 50, so that when the cover member 50 is mounted to the base housing body 10, the outer surface of the tapered supporting member 12 is pressed to be elastically deformed toward the notches 121. Here, in the present embodiment, the size value of the tapered supporting member 12 is larger than the size value of the corresponding position of the inner wall chamber of the cover member 50. The tapered supporting member 12 is provided with two notches 121 in the engaging direction in which the base housing body 10 is inserted into the cover member 50, so that the portion of the tapered supporting member 12 provided with the notches 121 forms an elastic wall that can swing toward the notches 121. When the tapered supporting member 12 is inserted into the cover member 50, the elastic wall is pressed to move toward the inside of the notches 121, and the elastic wall is closely fitted to the inner wall of the cover member 50 under the elastic restoring force, thereby further facilitating mounting the cover member 50 to the base housing body 10 and further enhancing the connection strength between the cover member 50 and the base housing body 10 at the same time.

Specifically, as shown in FIG. 2, in the embodiment of the present invention, the cover member 50 is provided with two air inlets 52, the two notches 121 are communicated with the outside airflow through the two air inlets 52, respectively, the base housing body 10 is provided with an airflow passage 16, one end of the airflow passage 16 is in fluid communication with the two notches 121, and the other end is in fluid communication with an internal chamber of the heating device 30 for providing a working airflow to the heating device 30. Here, in the present embodiment, the cover member 50 is provided with two air inlets 52, and the base housing body 10 is provided with an airflow passage 16. Air passing holes 1211 communicated with the airflow passage 16 are provided in the two notches 121. When the cover member 50 is mounted to the base housing body 10, the external airflow enters the notch 121 from the air inlet 52, and then enters the airflow passage 16 through the air passing hole 1211 to flow into the inner wall chamber of the heating device 30 for providing a working airflow to the heating device 30.

Specifically, as shown in FIG. 2, in the embodiment of the present invention, the base housing body 10 is provided with an oil storage chamber 15 arranged within the mounting cavity 11, the heating device 30 comprises a heating base 34 and an air outlet pipe, the heating base 34 is provided with an atomizing chamber 341 in fluid communication with the airflow passage 16 and an oil guiding hole 342 is in fluid communication with the atomizing chamber 341, the air outlet pipe is mounted to the heating base 34 and is in fluid communication with the atomizing chamber 341, when the heating device 30 is mounted to the mounting cavity 11, the oil guiding hole 342 is in fluid communication with the oil storage chamber 15, and the air outlet pipe extends out of the base housing body 10 to form the manipulation piece 31. Here, in the present embodiment, the heating device 30 comprises a heating base 34 and an air outlet pipe fixedly mounted to the heating base 34. The heating base 34 is provided with an atomizing chamber 341 and a heating element therein. The tobacco liquid in the oil storage chamber 15 flows into the atomizing chamber 341 through the oil guiding hole 342, and the heating element heats the tobacco liquid in the atomizing chamber 341 when being driven by the electric power of the battery device to generate smoke. The air outlet pipe is hollow, and one end of the air outlet pipe is in fluid communication with the atomizing chamber 341, and the other end passes outside the base housing body 10 to form a manipulation piece 31. The connecting portion 51 provided by the cover member 50 has a through hole to form a suction port 53 for the user to smoke. By arranging the manipulation piece 31 through the air outlet pipe, it eliminates the need to additionally provide a different discrete the manipulation piece, thereby effectively saving the internal occupied space and reducing the product volume while facilitating portability.

Further, as shown in FIG. 3, in the embodiment of the present invention, the heating base 34 is provided with an air inlet 343, the limiting seat 33 is provided with an air inlet passage 332, when the heating base 34 is mounted to the limiting seat 33, the air inlet passage 332 is communicated with the air inlet 343, and when the heating device 30 is mounted to the mounting cavity 11, the limiting seat 33 is partially inserted into the airflow passage 16 of the base housing body 10, so that the airflow passage 16 is in fluid communication with the air inlet 343 through the air inlet passage 332. Here, it can be understood that the suction port 53 of the electronic cigarette 1000 is generally provided such that the top end is prevented from being contaminated by external debris. In the present embodiment, the outer circumference of the end of the heating base 34 away from the air outlet pipe is provided with an air inlet 343, and the limiting seat 33 is provided with an air inlet passage 332. When the limiting seat 33 is sleeved to the heating base 34, the air inlet passage 332 is communicated with the air inlet 343, and the limiting seat 33 is further provided with an air guiding column 331 communicated with the air inlet passage 332. When the heating device 30 is mounted to the base housing body 10, the air guiding column 331 is engaged into the airflow passage 16 provided in the base housing body 10. Therefore, the external air flows into the notch 121 through the air inlet 52, flows into the airflow passage 16 through the air passing hole 1211, and finally flows into the air inlet passage 332 through the air guiding column 331 to be communicated with the air inlet 343 of the heating base 34 to form a manner that air enters from the top of the electronic cigarette 1000. Therefore, when the user smokes, under the force of gravity, the tobacco liquid cannot flow into the air passing hole 1211 through the airflow passage 16, thereby effectively preventing the phenomenon that the atomizer 100 leaks oil into the battery device to damage the electronic components inside the battery device.

It can be understood that, in some embodiments, the airflow passage 16 can be provided with two air guiding pipes in the base housing body 10. One end of the two air guiding pipes is communicated with the two air passing holes 1211, and the other end is communicated with the two air guiding columns 331 to form two independent airflow channels 16. Two air guiding pipes are also provided inside the base housing body 10. One end of the two air guiding pipes is communicated with the air guiding column 331 after being communicated with each other, and the other end is communicated with the two air passing holes 1211 to form the airflow passage 16. The above manner is within the scope of protection of the present invention.

Figure 5:
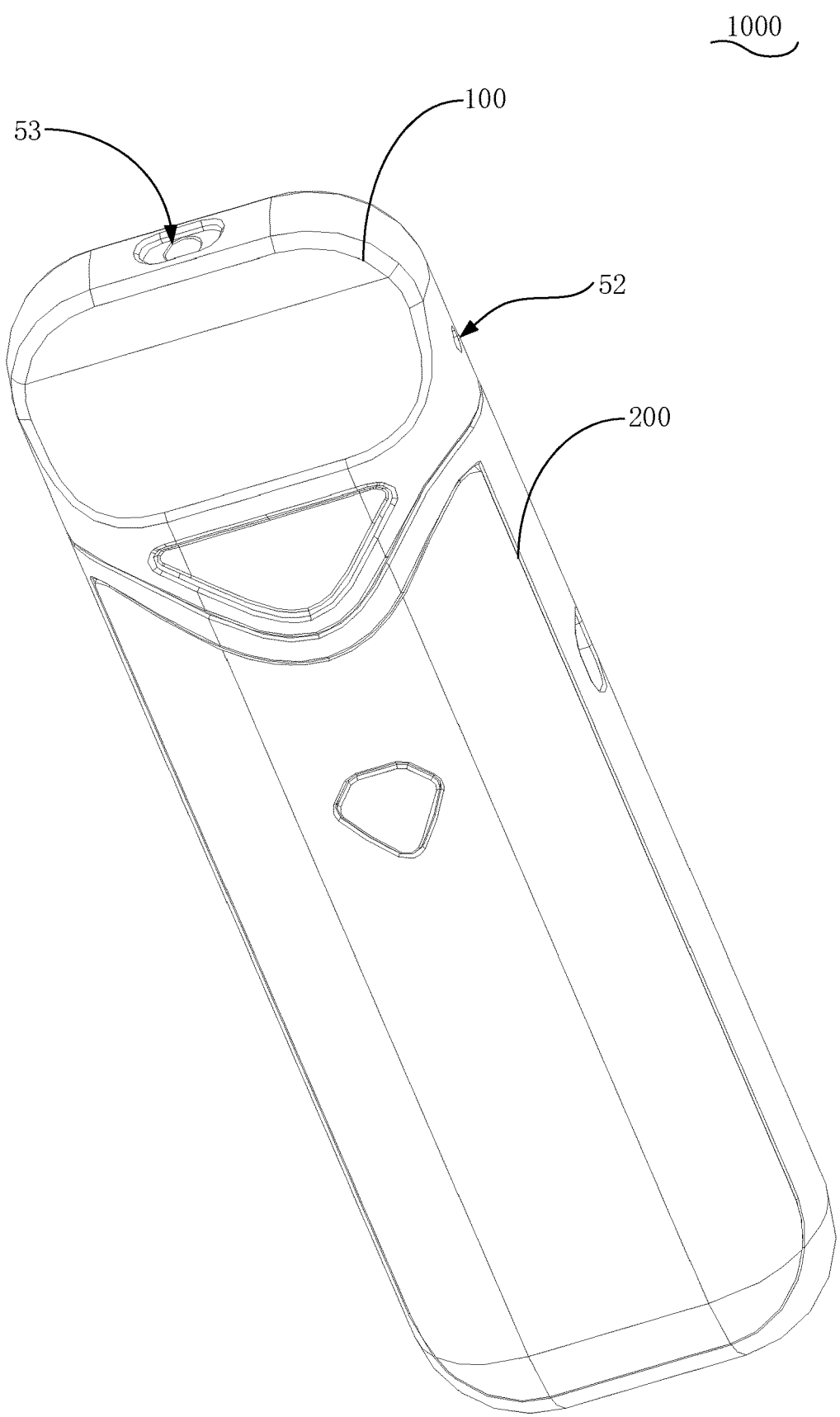
FIG. 5 is a perspective schematic diagram of an electronic cigarette according to the present invention.

Referring to FIG. 5, the present invention further provides an electronic cigarette 1000. The electronic cigarette 1000 comprises a battery device and an atomizer 100 of the electronic cigarette 1000. Refer to the above embodiment for the specific structure of the atomizer 100 of the electronic cigarette 1000. Due to the use of all the technical solutions of all the above embodiments, the electronic cigarette 1000 has at least all the beneficial effects brought by the technical solutions of the above embodiments, which will not be described in detail herein.

The above are preferred embodiments of the present invention merely and are not intended to limit the patent scope of the present invention. Any equivalent structures made according to the description and the accompanying drawings of the present invention without departing from the idea of the present invention, or any equivalent structures applied in other relevant technical fields directly or indirectly are intended to be included in the patent protection scope of the present invention.

What is claimed is:

1. An atomizer for an electronic cigarette, comprising:
   a base housing body defining a mounting cavity and an exit hole,
   a heating device comprising a manipulation piece defining a first end of the heating device and a limiting seat defining a second end of the heating device, the first and second ends being opposite sides of the heating device, and
   a cover member detachably mounted to the base housing body and is configured for covering the manipulation piece, wherein;
   the manipulation piece is partially arranged within the mounting cavity and partially extending past the exit hole, the manipulation piece at least partially defining an air outlet pipe,
   the limiting seat is coupled to the mounting cavity,
   the cover member defines a connecting portion that is arranged such that when the cover member is mounted to the base housing body, the connecting portion is engaged with the manipulation piece for coupling the cover member with the manipulation piece, and when the cover member is separated from the base housing body, the manipulation piece is disengaged from the connecting portion, and
   one of the connecting portion and the manipulation piece defines an engaging groove, and the other of the connecting portion and the manipulation piece is provided with a first elastic sealing ring on a part of an outer peripheral surface thereof such that the seating ring abuts an inner groove wall of the engaging groove when the connecting portion and the manipulation piece are coupled.

2. The atomizer for an electronic cigarette according to claim 1, wherein the limiting portion is defined and arranged at a transition between the heating device and the manipulation piece, the base housing body defining a limiting groove into which a part of the limiting portion is engaged such that when the heating device is mounted within the mounting cavity, the manipulation piece extends out of the base housing body through the exit hole, and the limiting portion is elastically clamped in the limiting groove such that the heating device is limited to being arranged within the mounting cavity.

3. The atomizer for an electronic cigarette according to claim 1, wherein when the heating device is mounted to the mounting cavity, an outer peripheral surface of the limiting seat abuts an inner wall of the mounting cavity.

4. The atomizer for an electronic cigarette according to claim 1, wherein the base housing body further defines tapered supporting members, each arranged at both sides and adjacent to the manipulation piece such that an outer peripheral surface of the tapered supporting members are closely fitted to an inner wall of the cover member for the cover member to be detachably mounted to the base housing body.

5. The atomizer for an electronic cigarette according to claim 4, wherein the thickness of each of the tapered supporting members is gradually increased from an end of the supporting members arranged furthest away from the base housing body towards an end of the supporting members arranged closest to the base housing body; and/or the tapered supporting members are provided with two notches in an engaging direction in which the base housing body is inserted into the cover member, such that when the cover member is mounted to the base housing body, an outer surface of the tapered supporting members are elastically deformed towards the two notches.

6. The atomizer for an electronic cigarette according to claim 5, wherein the cover member defines two air inlets, the two notches are in fluid communication with the outside airflow through the two air inlets, respectively, the base housing body further defines an airflow passage, with one end of the airflow passage in fluid communication with the two notches, and the other end of the airflow passage in fluid communicated with an internal chamber of the heating device for providing an airflow to the heating device.

7. The atomizer for an electronic cigarette according to claim 1, wherein the base housing body further comprises an oil storage chamber that is arranged within the mounting cavity, the heating device comprises a heating base and the air outlet pipe, the heating base comprising an atomizing chamber in fluid communication with the airflow passage and an oil guiding hole in fluid communication with the atomizing chamber, the air outlet pipe is mounted to the heating base and in fluid communication with the atomizing chamber when the heating device is mounted within the mounting cavity, the oil guiding hole is in fluid communication with the oil storage chamber, and the air outlet pipe at least partially extends out of the base housing body to form the manipulation piece.

8. An electronic cigarette, comprising an atomizer which comprises
a base housing body defining a mounting cavity and an exit hole,
a heating device comprising a manipulation piece defining a first end of the heating device and a limiting seat defining a second end of the heating device, the first and second ends being opposite sides of the heating device, and
a cover member detachably mounted to the base housing body and is configured for covering the manipulation piece, wherein:

the manipulation piece is partially arranged within the mounting cavity and partially extending past the exit hole, the manipulation at least partially defining an air outlet pipe,
the limiting seat is coupled to the mounting cavity,
the cover member defines a connecting portion that is arranged such that when the cover member is mounted to the base housing body, the connecting portion is engaged with the manipulation piece for coupling the cover member with the manipulation piece, and when the cover member is separated from the base housing body, the manipulation piece is disengaged from the connecting portion, and
one of the connecting portion and the manipulation piece defines an engaging groove, and the other of the connecting portion and the manipulation piece is provided with a first elastic sealing ring on a part of an outer peripheral surface thereof such that the sealing ring abuts an inner groove wall of the engaging groove when the connecting portion and the manipulation piece are coupled.

9. The electronic cigarette according to claim 8, wherein a limiting portion is defined and arranged at a transition between the heating device and the manipulation piece, the base housing body defining a limiting groove into which a part of the limiting portion is engaged such that when the heating device is mounted within the mounting cavity, the manipulation piece extends out of the base housing body through the exit hole, and the limiting portion is elastically clamped in the limiting groove such that the heating device is limited to being arranged within the mounting cavity.

10. The electronic cigarette according to claim 8, wherein when the heating device is mounted to the mounting cavity, an outer peripheral surface of the limiting seat abuts an inner wall of the mounting cavity.

11. The electronic cigarette according to claim 8, wherein the base housing body further defines a tapered supporting members, each arranged at both sides and adjacent to the manipulation piece such that the outer peripheral surface of the tapered supporting members are closely fitted to an inner wall of the cover member for the cover member to be detachably mounted to the base housing body.

12. The atomizer for an electronic cigarette according to claim 11, wherein the thickness of each of the tapered supporting members is gradually increased from an end of the supporting members arranged furthest away from the base housing body towards an end of the supporting members arranged closest to the base housing body; and/or the tapered supporting members are provided with two notches in an engaging direction in which the base housing body is inserted into the cover member, such that when the cover member is mounted to the base housing body, an outer surface of the tapered supporting members are elastically deformed towards the two notches.

13. The atomizer for an electronic cigarette according to claim 12, wherein the cover member defines two air inlets, the two notches are in fluid communication with the outside airflow through the two air inlets, respectively, the base housing body further defines an airflow passage, with one end of the airflow passage in fluid communication with the two notches, and the other end in fluid communication with an internal chamber of the heating device for providing a working airflow to the heating device.

14. The atomizer for an electronic cigarette according to claim 8, wherein the base housing body further comprises an oil storage chamber that is arranged within the mounting cavity, the heating device comprises a heating base and the air outlet pipe, the heating base comprising an atomizing chamber in fluid communication with the airflow passage and an oil guiding hole in fluid communication with the atomizing chamber, the air outlet pipe is mounted to the heating base and in fluid communication with the atomizing chamber when the heating device is mounted within the mounting cavity, the oil guiding hole in fluid communication with the oil storage chamber, and the air outlet pipe at least partially extends out of the base housing body to form the manipulation piece.

* * * * *